(12) United States Patent
Reihl et al.

(10) Patent No.: US 7,747,644 B1
(45) Date of Patent: Jun. 29, 2010

(54) INTERNET DELIVERY SYSTEM DELIVERING ELECTRONIC INFORMATION PRODUCTS TO A PURALITY OF USERS ACCORDING TO USER AUTHENTICATION AND TYPE OF USER

(75) Inventors: Jeffrey Raymond Reihl, Parker, CO (US); David Ray King, Castle Rock, CO (US); David Martin Nelson, Parker, CO (US); Larry Jay Browder, Jr., Highlands Ranch, CO (US); Vineet Shriniwas Joshi, Denver, CO (US); Brian David Horblit, Centennial, CO (US)

(73) Assignee: Thomson Healthcare Inc., Ann Arbor, MI (US)

( * ) Notice: Subject to any disclaimer, the term of this patent is extended or adjusted under 35 U.S.C. 154(b) by 300 days.

(21) Appl. No.: 10/675,235

(22) Filed: Sep. 30, 2003

(51) Int. Cl.
*G06F 7/00* (2006.01)
(52) U.S. Cl. .................. 707/783; 707/784; 707/785; 707/786
(58) Field of Classification Search .............. 707/1, 707/3–5, 7–10, 100–104.1, 200–204; 705/8, 705/14, 28; 709/200–203, 217–219, 238; 715/530
See application file for complete search history.

(56) References Cited

U.S. PATENT DOCUMENTS

| | | |
|---|---|---|
| 5,734,883 A | 3/1998 | Umen |
| 5,903,889 A | 5/1999 | De La Huerga |
| 5,950,632 A | 9/1999 | Reber |
| 6,411,836 B1 * | 6/2002 | Patel et al. .................. 600/407 |
| 6,871,221 B1 * | 3/2005 | Styles .......................... 709/221 |
| 2001/0037241 A1 * | 11/2001 | Puri ............................. 705/14 |
| 2001/0054114 A1 * | 12/2001 | DuVal et al. ................. 709/247 |
| 2002/0007287 A1 | 1/2002 | Straube et al. |
| 2002/0023230 A1 * | 2/2002 | Bolnick et al. .............. 713/202 |
| 2002/0103008 A1 * | 8/2002 | Rahn et al. .................. 455/557 |
| 2002/0104018 A1 * | 8/2002 | Singhani et al. ............. 713/201 |
| 2002/0165752 A1 * | 11/2002 | Miller ........................... 705/8 |
| 2003/0004984 A1 * | 1/2003 | Chou ........................... 707/500 |
| 2003/0167315 A1 * | 9/2003 | Chowdhry et al. .......... 709/218 |
| 2003/0233586 A1 * | 12/2003 | Urakami et al. ............. 713/202 |

FOREIGN PATENT DOCUMENTS

WO    WO01/45015    6/2001

* cited by examiner

*Primary Examiner*—Cheyne D Ly
(74) *Attorney, Agent, or Firm*—Faegre & Benson LLP

(57) ABSTRACT

An Internet delivery method delivers electronic information products to a plurality of users via the Internet. A plurality of display formats are stored in a database. The display formats including at least a default display format and a custom display format. Information is also stored for each user indicating whether the user is a specific type of user. When a user logs in, the user is identified as being that specific type of user. If the user is identified as the specific type of user, then an electronic information product is delivered to the user in the custom display format. The electronic information products are accessed via computers connected to the Internet, including wireless devices.

35 Claims, 15 Drawing Sheets

INTERNET DELIVERY SYSTEM DELIVERING ELECTRONIC INFORMATION PRODUCTS TO A PURALITY OF USERS ACCORDING TO USER AUTHENTICATION AND TYPE OF USER

COPYRIGHT NOTICE

A portion of this patent document contains material which is subject to copyright protection. The copyright owner has no objection to the facsimile reproduction by anyone of the patent document, as it appears in the Patent and Trademark Office patent files or records, but otherwise reserves all copyright rights whatsoever.

RELATED APPLICATIONS

This application is related to the following pending applications, each of which is hereby incorporated by reference in its entirety:

U.S. patent application Ser. No. 10/289,782 titled ELECTRONIC DOCUMENT REPOSITORY MANAGEMENT AND ACCESS SYSTEM, filed Nov. 20, 2002; and U.S. patent application Ser. No. 10/675,236, titled NETWORK-BASED METHOD AND SYSTEM FOR MANAGING AND PROVIDING ACCESS TO A FORMULARY, filed concurrently herewith.

BACKGROUND OF THE RELATED ART

The invention relates generally to information technology. More particularly, the invention relates to methods and systems capable of managing and delivering a plurality of different information services or applications over the Internet.

The growth in the use of computers, particularly in connection with the Internet and electronic commerce, has led to an increased availability of and improved accessibility to information delivered over the Internet. In particular, electronic databases for research purposes or obtaining information have become a research resource preferred to traditional print databases. However, existing Internet delivery methods and systems are often customized for a single individual information service or application, or for a specific operating system, computer platform, technology or architecture. They often do not interconnect or support future information services or applications. In particular, the architectures of existing Internet delivery methods and system are not flexible enough to support functionality which may later be desired to be added to the information service or application.

Furthermore, existing Internet delivery methods and systems are provided in a rigid format such that every subscriber is offered the same display or user interface. Different individual or group subscribers cannot alter their display or user interface to provide a customized view or functionality. This limitation prevents the customization and optimization of a single Internet delivery method or system for use by multiple subscribers having varying needs or concentrations.

Also, it may be awkward for customers to use Internet delivery methods and systems that are developed independently, use different technologies and architectures and/or present different user interfaces. Supporting several different technology suites and several different information services or applications performing similar functions may be an inefficient use of development, quality assurance, content mastering, and operational resources. Supporting multiple information services or applications developed without a common business or technical vision also makes it much more difficult to build new applications or application functions, particularly those functions that span several different information services or applications.

BRIEF SUMMARY

The preferred embodiments of the present invention address the issues discussed above, and relate to an improved flexible Internet delivery system and method capable of offering a full suite of information services and applications while still providing development and maintenance delivery system. Information services and applications can be added using a common architecture and application framework, while different individual or group subscribers can nevertheless alter their display or user interface to provide a customized view or functionality.

According to a first aspect of the invention, an Internet delivery method delivers electronic information services or applications to a plurality of users via the Internet. A plurality of display formats are stored in a database. The display formats including at least a default display format and a custom display format. Information is also stored for each user indicating whether the user is a specific type of user. When a user logs in, the user is identified as being that specific type of user. If the user is identified as the specific type of user, then an electronic information product is delivered to the user in the custom display format.

BRIEF DESCRIPTION OF THE DRAWINGS

The figures of the accompanying drawings are meant to be exemplary and not limiting, in which like references are intended to refer to like or corresponding parts, and in which.

DETAILED DESCRIPTION

Figure 1:
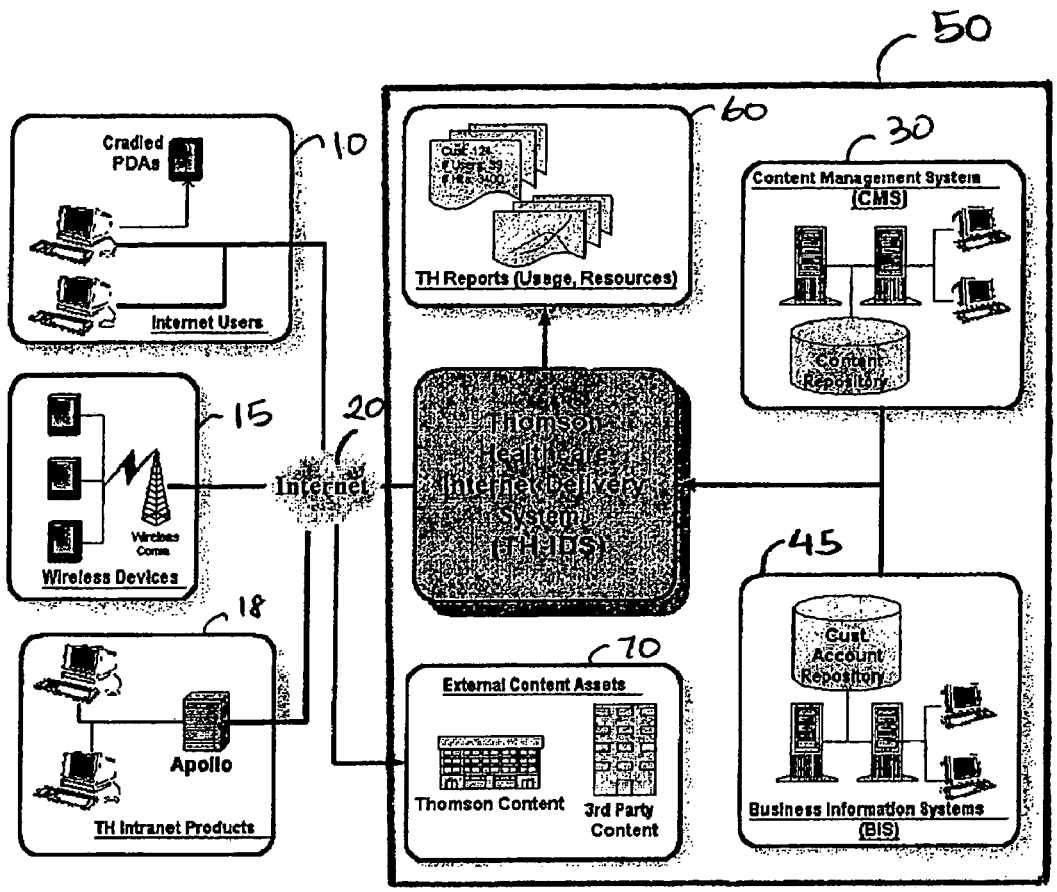
FIG. 1 is a diagram of an Internet Delivery System according to an embodiment of the invention.

Preferred embodiments of the invention are now described with reference to the drawings. The basic architecture of an Internet delivery system according to an embodiment of the present invention is shown in FIG. 1. Some of the system and components of the system as presented in FIG. 1 are exemplary of the West electronic document repository management and access system, available from West Publishing Company, of Eagen, Minn. and further described in U.S. patent application Ser. No. 10/289,782 filed on Nov. 20, 2002 and titled ELECTRONIC DOCUMENT REPOSITORY MANAGEMENT AND ACCESS SYSTEM, which is incorporated herein by reference in its entirety.

The system and components of Internet Delivery System 50 as presented in FIG. 1 include content management system 30, business information systems 45, reports 60 and external content assets 70. Electronic information products are delivered to the users of computers 10, wireless devices 15 and/or Intranet products 18 via Internet 20. These electronic information products are information services or applications offered to customers in exchange for payment or some other business purpose. The computer 10 may be any desktop, laptop, personal digital assistant (PDA) or other computer known in the art or hereafter developed. Known computers generally includes components such as one or more central processing units (CPU), processors, storage, modules, drives, monitors, displays, and/or keyboards. The wireless devices 15 may be any wireless PDAs or mobile telephones known in the art or hereafter developed. The Intranet products 18 may be any Intranet known in the art, such as the Apollo system from Thomson Healthcare, or hereafter developed. The computer 10, wireless device 15 and/or Intranet products 18 provide a user with access to the Internet delivery system 50. Although two computers 10, three wireless devices 15 and two computers in the Intranet products 18 are shown in FIG. 1 and discussed hereafter, for the sake of simplicity, there may be any number of computers and/or wireless devices and users.

The preferred embodiments of the invention do not require any alteration in the operation of Internet 20.

The Internet delivery system 50 described herein provides a flexible architecture for delivering a plurality of electronic information products, such as the formulary tool described in U.S. patent application Ser. No. 10/675,236, titled NETWORK-BASED METHOD AND SYSTEM FOR MANAGING AND PROVIDING ACCESS TO A FORMULARY, filed concurrently herewith. The products delivered over the Internet delivery system 50 include for example, electronic information products and/or functionality relating to healthcare, for example, pharmaceutical inventory management, formulary management, continuing medical education, web community services, advertising, or electronic commerce such as web based pharmaceutical order and delivery. The electronic information products may be developed prior to or at the same time the Internet delivery system 50 is provided, or embedded and/or incorporated into the system 50 later to provide new or additional products or functionality. Each of the electronic information products may be provided access to and/or incorporate existing content or databases to maximize the utilization and flexibility of product delivery over the system 50. Additionally, the electronic information products may be customizable by the system provider, administrative subscriber or individual subscriber to provide customized features such as, the user interface appropriate to the organization or particular role within the organization, or other functionality necessary to the subscriber or group.

The content management system 30 contains data or other information in a content repository, as further described herein. The business information systems 45 preferably provide, for example, associating customer account information with a user, for example, user type, product subscriptions, and other data or other information relating to customer accounts.

Figure 8:
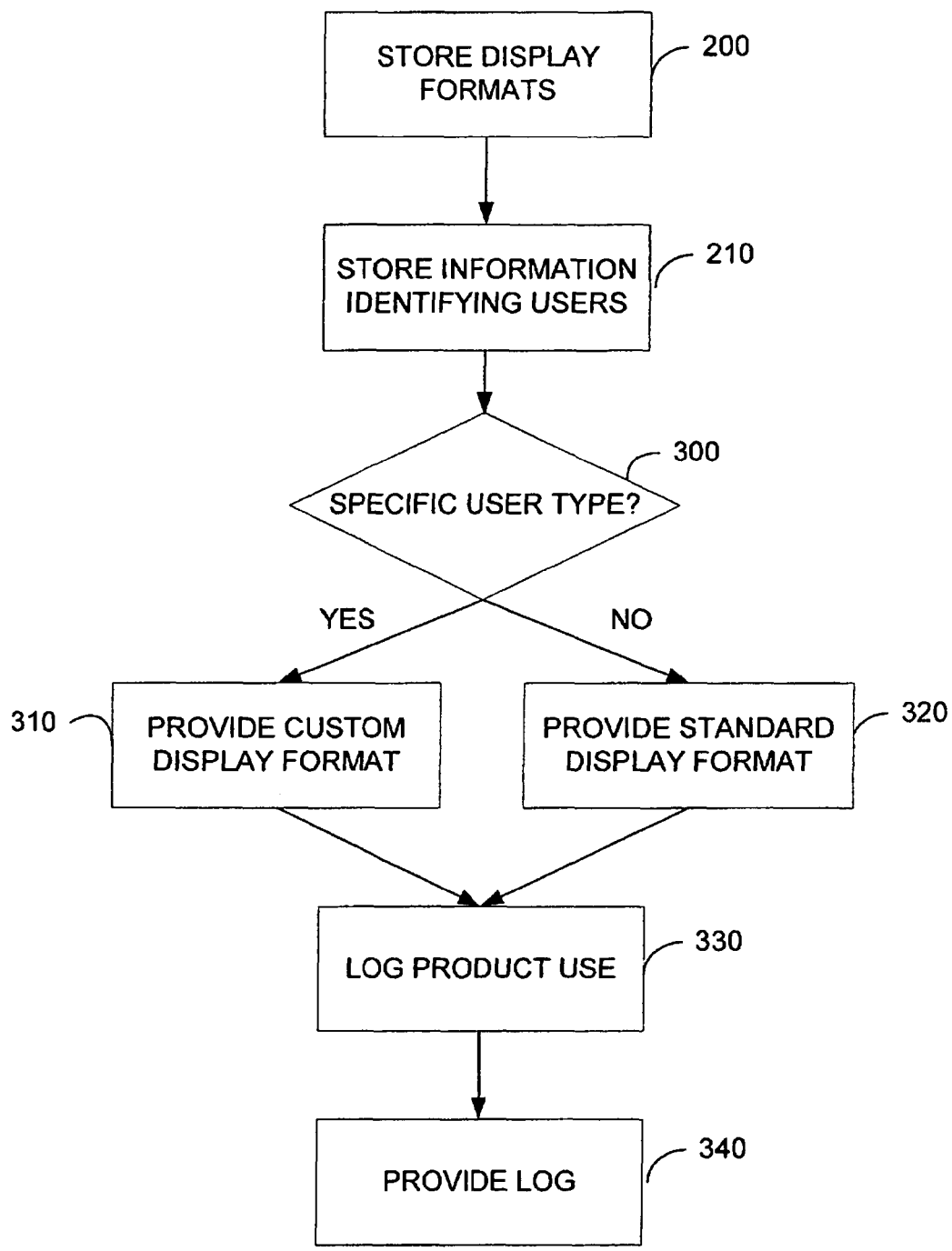
FIG. 8 is a flowchart of a method for identifying users, providing display formats, and logging subscriber use of the method and system according to an embodiment of the invention.

The Internet delivery system 50 generates reports 60 to provide information regarding usage and resources of the system 50, as further described herein in reference to FIG. 8.

In a preferred embodiment, the content management system 30 is configured as a relational database. The content management system 30 includes healthcare related information such as the Physicians Desk Reference, proprietary pharmaceutical databases, or other healthcare information. Data items or documents in the database are originally gathered and processed according to an intake process, which may include enhancing the document with such features as described in U.S. patent application Ser. No. 10/289,782 titled ELECTRONIC DOCUMENT REPOSITORY MANAGEMENT AND ACCESS SYSTEM, filed Nov. 20, 2002, such as assigning each document a unique identifier, providing hyperlinks in the text to related information, adding editorial notes, associating metafiles to enrich documents, or associating the document into a particular category, subcategory or table of contents hierarchy.

Figure 2:
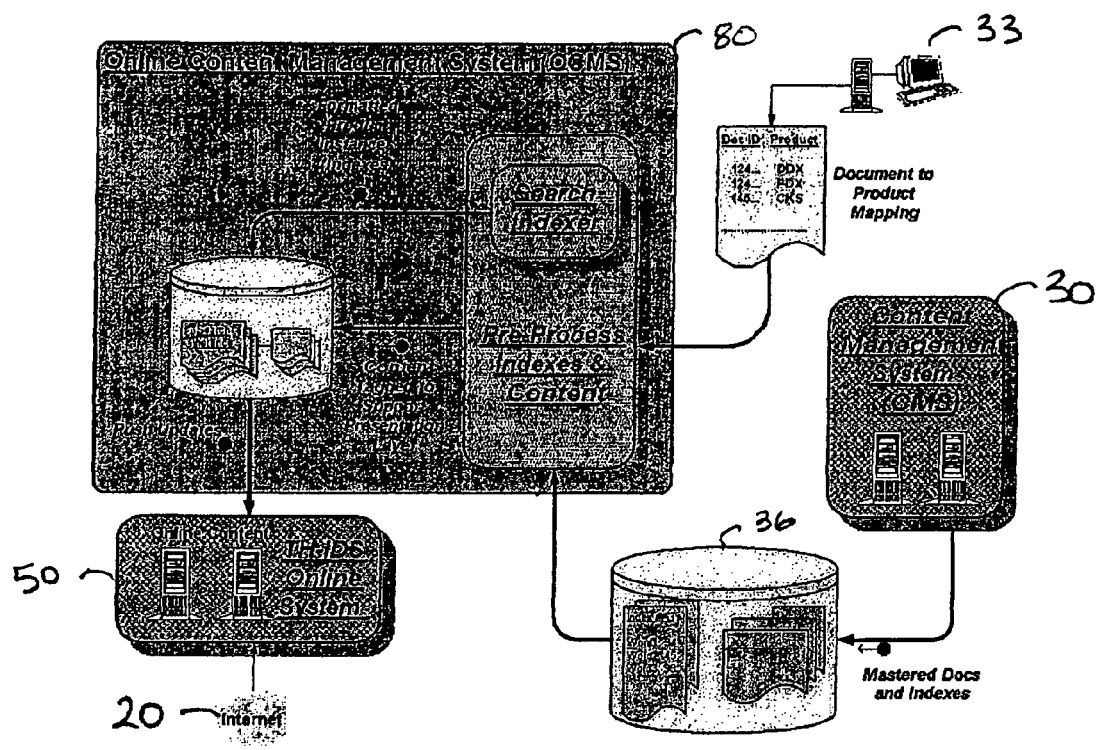
FIG. 2 is a diagram of a content management system according to an embodiment of the invention.

Preferably, an online content management system 80 enhances data items or documents according to the process depicted in FIG. 2. Online content may be produced from the data items or information in the database by combining document to product mapping 33 and master documents and indexes 36 in content management system 30. Document to product mapping 33 preferably includes assigning an identifier, such as an identification number to each document, and assigning the document identification number to a particular product. This provides the ability to limit the data offered or included in each product provided by the system 50. For example, delivery of a formulary product over the system 50 is limited to users subscribing to the formulary product. Indexes and master documents 36 are pre-processed to product content and tagged to support the presentation layer. The online content management system 80 combines the content with search instances and pushes updates to the online system, for user access over the Internet 20.

Figure 3:
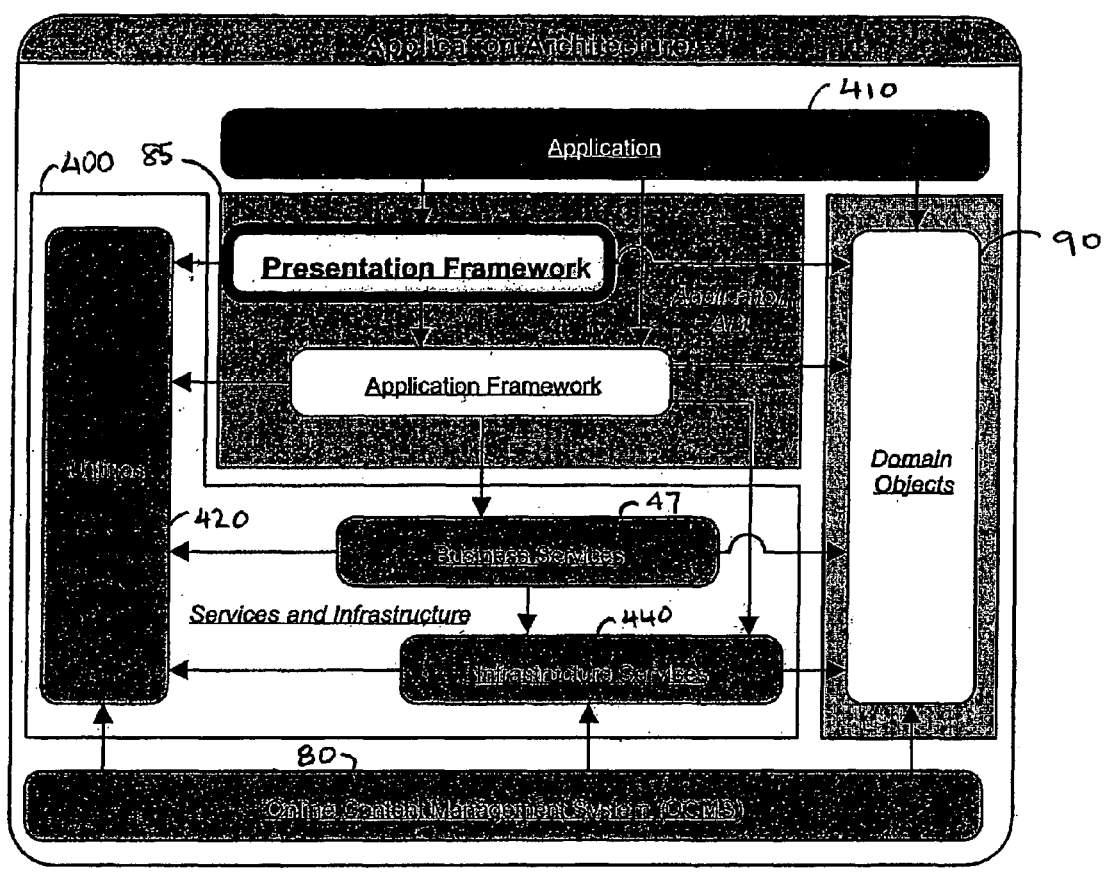
FIG. 3 is a diagram of an application architecture according to an embodiment of the invention.

Referring to FIG. 3, which depicts a high level view of the application architecture of the online system 50 according to a preferred embodiment, the online system 50 includes the application 410 and underlying application program interface (API) 85, domain objects 90, services and infrastructure 400, and is connected to online content management system 80. The API 85 includes the presentation framework 460 and application framework 450 which provide, for example, support of screen navigation and common page behavior, in a consistent and reliable manner to provide a seamless delivery system for more than one product. For example, web page templates may be pre-produced and content for a particular product is embedded into the pre-existing templates. The application API 85 may be designed using existing software, such as Java Developer, or other known software, or software developed hereafter. The application framework 450 is accessed as an interface to the underlying services, which enables evolution of the system 50 services without individually customizing each product or function delivered over the system 50. The presentation framework 460 may provide a common presentation for each product, or provide a customized presentation for a product. The application 410 and API 85 access information that is shared by the layers of the system using common domain objects 90. The domain objects 90 encapsulate common behavior utilized over each layer so as to eliminate the need for redundant objects within each layer, including for example, user information such as rights or preferences, such as how content is retrieved and displayed or how the product interface is displayed; logical and physical session data relevant to each user; parameters required to perform a search request; search result parameters such as document product; version and document ID; document request parameters required to retrieve a single document; document data; document outline objects describing the structure of a document; user data, including entity level user, user group or individual user data objects containing data specific to the user of an application; authorization request objects for querying the access control system about a specific set of resources or products and returning authorization information about the resource or product; product information, including content sets and fields within the content sets; and exceptions, such as error interpretation.

Still referring to FIG. 3, in a preferred embodiment, the services and infrastructure 400 includes utilities 420, business services 47, and infrastructure services 440. The utilities 420 are common utilities that may be used by various products, for example, file access routines or preference manipulation. Use of common utilities reduces the need for redundant product specific development work for each product delivered over the system 50. The business services 47 are services including search, access control or retrieval of content in the content management system 30. The infrastructure services 440 include for example monitoring, logging or tracking usage, and data access and reporting.

Figure 4:
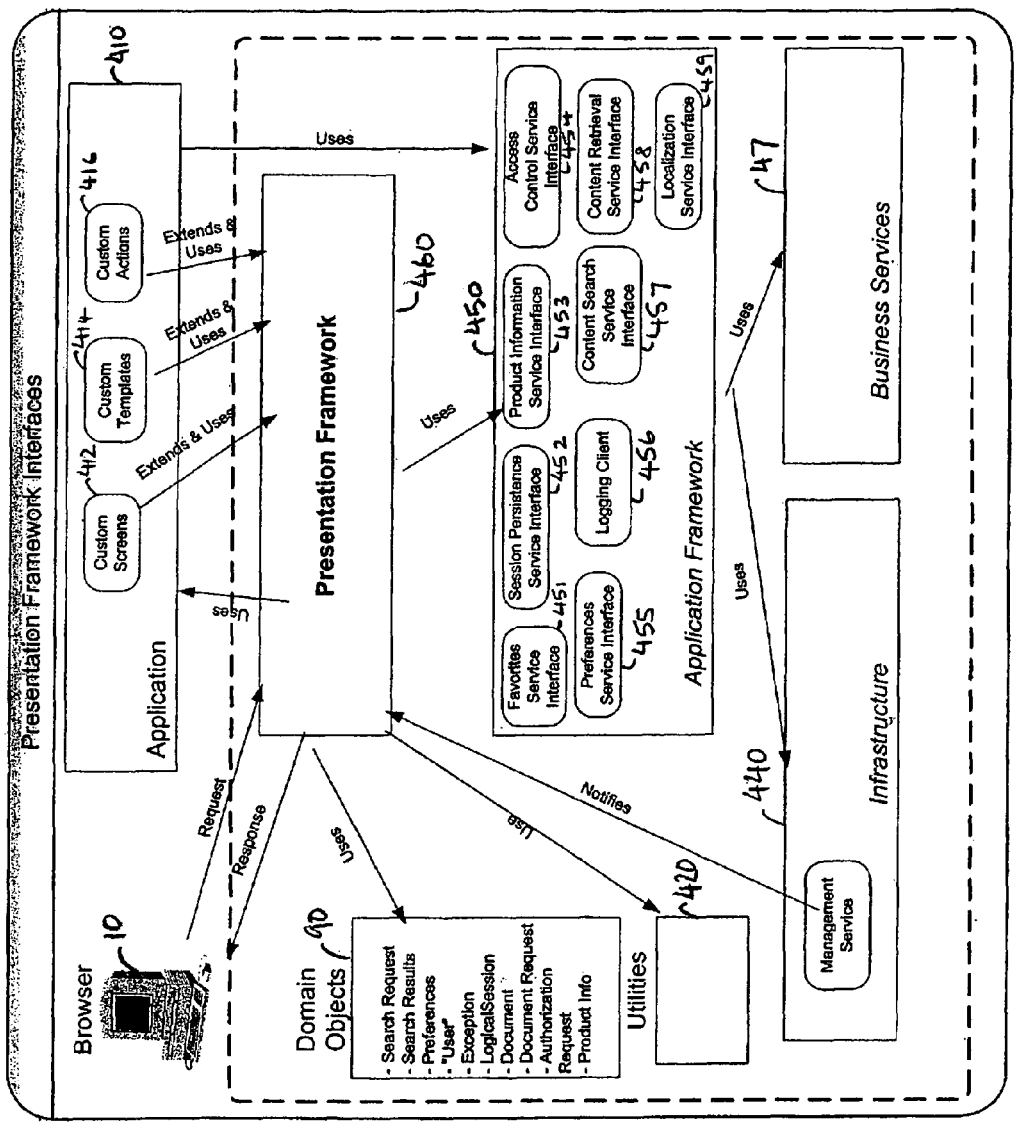
FIG. 4 is a diagram of the presentation framework interfaces according to an embodiment of the invention.
Figure 5:
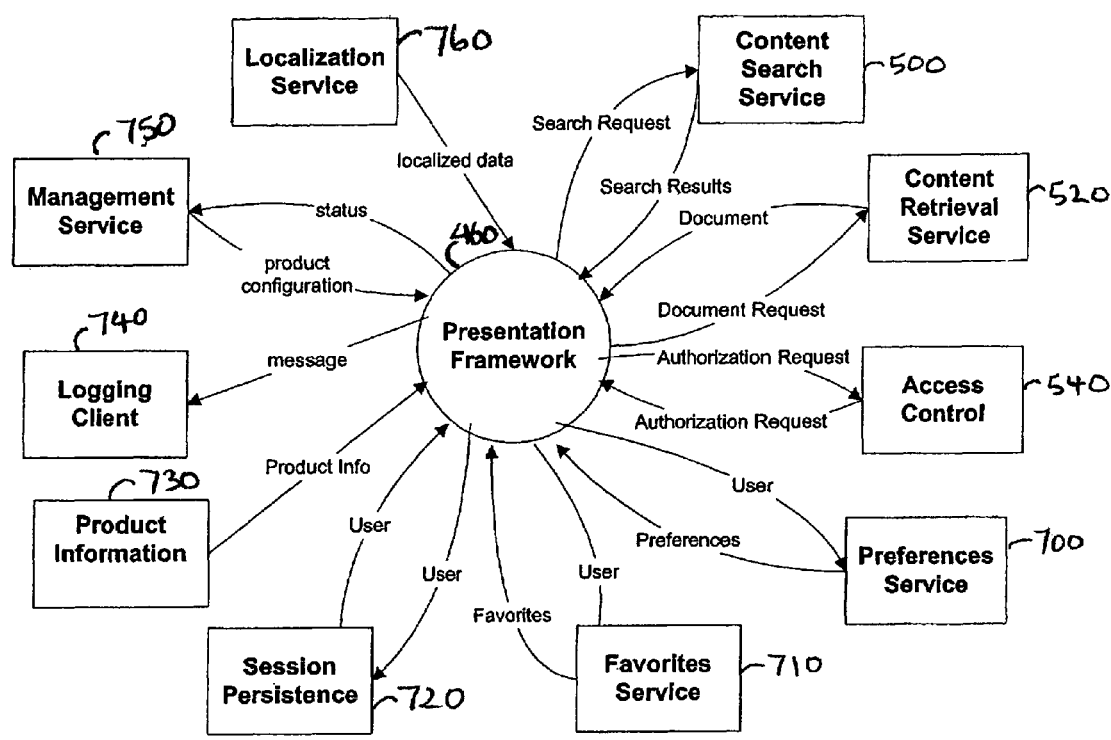
FIG. 5 is a dataflow diagram for a presentation framework according to an embodiment of the invention.

Referring to FIGS. 4 and 5, which depicts a detailed view of the presentation framework interfaces, according to a preferred embodiment of the invention, with the components described in reference to FIG. 3. The application 410 contains custom screens 412, custom templates 414 and custom actions 416. The custom screens 412 contain presentation logic that prepares a page for display, including, for example, retrieving data and formatting data from the application framework 450. The custom templates 414 make up the page describing what is to be displayed. The templates may contain, for example HTML and Velocity tags that are needed to construct the page. The templates are used together with the presentation framework and product specific mark-up to provide the product display on a webpage. The custom actions 416 include for example application specific control logic for utilizing the presentation framework or the application framework. The application framework 450 is the path by which applications will communicate with the services they require. The preferred functionality of the presentation framework 450 is to provide smart proxies and application isolation. The presentation framework 460 utilizes each of the components included in the application 410 and the application framework 450 to provide consistent web page views of each of the products delivered over the system.

The application framework 450 includes interfaces such as the Favorites Service Interface 451, Product Information Service Interface 453, Access Control Service Interface 454, Preferences Service Interface 455, Logging Client 456, Content Search Service Interface 457, Content Retrieval Service Interface 458 and Localization Service Interface 459. The Favorites Service Interface 451 provides an interface between the between the presentation framework 460 and the Favorites Service 710, which provides a user's list of favorite searches. The user Favorites Service list is associated with the user so that each time the user accesses the system, the user has access to his or her list to expedite selecting a favorite product or item. The Product Information Service Interface 453 provides the interface between the presentation framework 460 and the Product Information 730 which provides information related to product structure. For example, the presentation framework 460 will obtain information about content sets for each product. The Access Control Service Interface 454 provides the interface between the presentation framework 460 and the Access Control System 540, which provides user authentication preferably using caching and routing and/or authorization requests, as further described herein. Additionally, the Access Control Service Interface 454 provides the interface between the presentation framework 460, which preserves the state of the user's session during intervals between expiration of a user's HTTP session and a user's logical session expires. All of the data associated with the user's session necessary for storage is stored to the user domain object.

The Preferences Service Interface 455 provides the interface between the presentation framework 460 and the Preferences Service 700 when a user domain object is needed. User domain objects typically are created during the login process. Preferences are obtained from the preferences service 700 and stored in the user object, and the user object is updated when user preferences change. The Logging Client interface 456 is a utility that interacts with the Logging Client 740 to log information needed by the presentation framework 460. The Content Search Service Interface 457 provides the interface between the presentation framework 460 and the content search service 500, further described herein, which provides searching system products. The Content Retrieval Service Interface 458 provides the interface between the presentation framework 460 and the content retrieval service 520 which receives application requests to retrieve documents or other items stored in the content database. The application typically requests items using a document identifier. The Localization Service Interface 459 provides the interface between the application framework 460 and the Localization Service 760 which provides product display views appropriate to a particular locality, for example, in a particular language.

Figure 6:
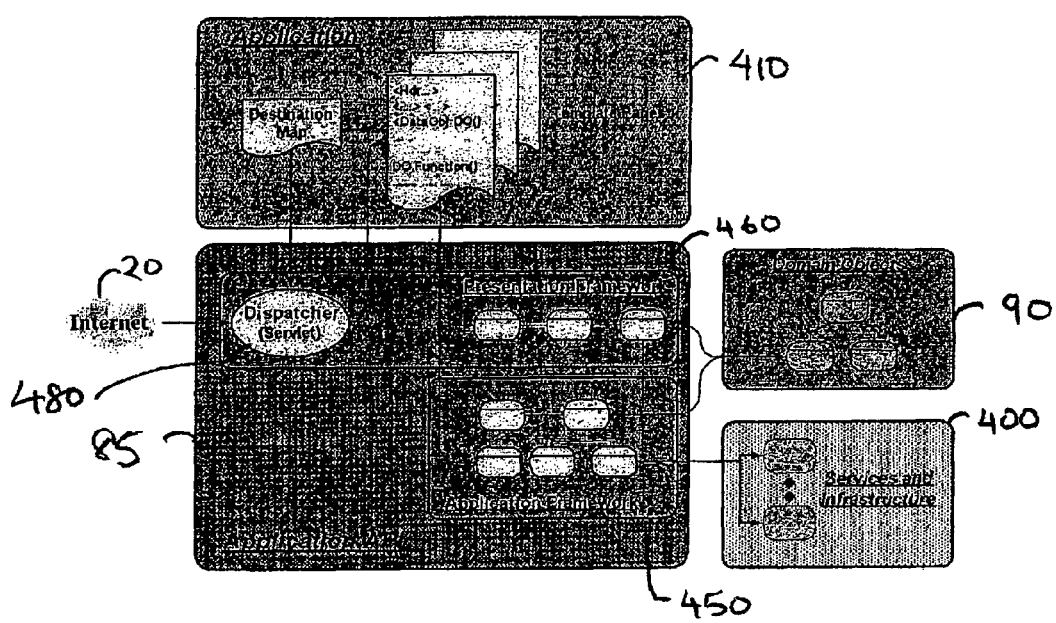
FIG. 6 is a diagram of the application presentation interface according to an embodiment of the invention.
Figure 7:
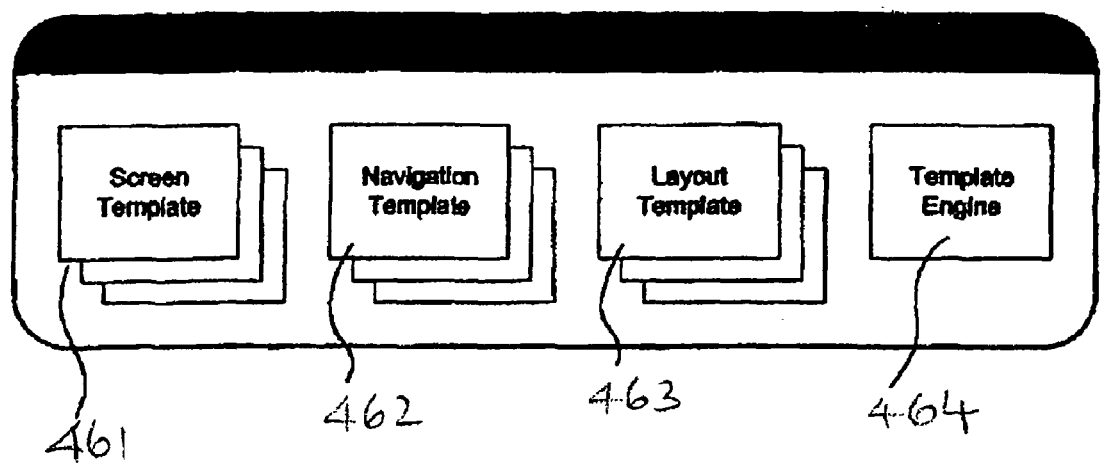
FIG. 7 depicts the templates and template engine in presentation framework 460 according to an embodiment of the invention.

Referring to FIGS. 6 and 7, in a preferred embodiment, the application 410 provides template pages, as further described herein, to provide a visual presentation of the system. The dispatcher servlet 480 controls which template page is accessed at each user request over the Internet 20. Specialized templates and screen classes format data for construction of the HTML pages that are sent to the presentation framework 460. Preferably, there is one screen class and one screen template for every screen view and presentation framework 460 uses a template engine and templates to create HTTP documents or document fragments. FIG. 7 shows screen template 461, navigation template 462, layout template 463, and template engine 464.

Referring to FIG. 8, which depicts a high level flowchart of a method for identifying a user, providing display formats and logging use of the system according to an embodiment of the invention, a user accesses the Internet delivery system by logging into the system. Log-in to the Internet delivery system generally includes accessing the system website and entering the user's subscription account information. The system determines whether the user is authorized based on the log-in information. Log-in information may include a subscription account name, user name or password, or other log-in procedure known in the art. In another embodiment of the invention, log in may be accomplished by Internet protocol (IP) address recognition, for example, using the user's IP address is an identifier known in the art for a computer or device on a TCP/IP network, such as a numeric address. If the system recognizes the user's IP address, the subscriber need not enter subscription account information, and the system will automatically determine whether the user is authorized based on the IP address. The system supports flexible subscription accounts, for example, organization based multiple user accounts having access to every database, product, product and function offered by the system, individual user subscriptions, pay-per-use, or select access to certain databases, products or functions. For example, only a user subscribing to or otherwise authorized to access the formulary database could obtain access to the formulary database resources, and search and retrieve data items. Subscribers may create user groups by region, facility, department or other logical grouping.

Display formats are stored to the system (step 200). For example, a plurality of customized display formats are provided for users according to, for example, user type or particular user. Information associated with each user, or user type is stored to the system (step 210). The information associated with each user may be for example user type, account information, subscription information, product access information, custom display format preferences; or user display preferences. If the user is identified, (step 300) as authorized and having user information associated with the user, such as custom display formats or user type, the user is provided a custom display format (step 310). If the user is not identified, the user is provided the default display format (step 320). If the user is not authorized, log in to the system fails.

Figure 9A:
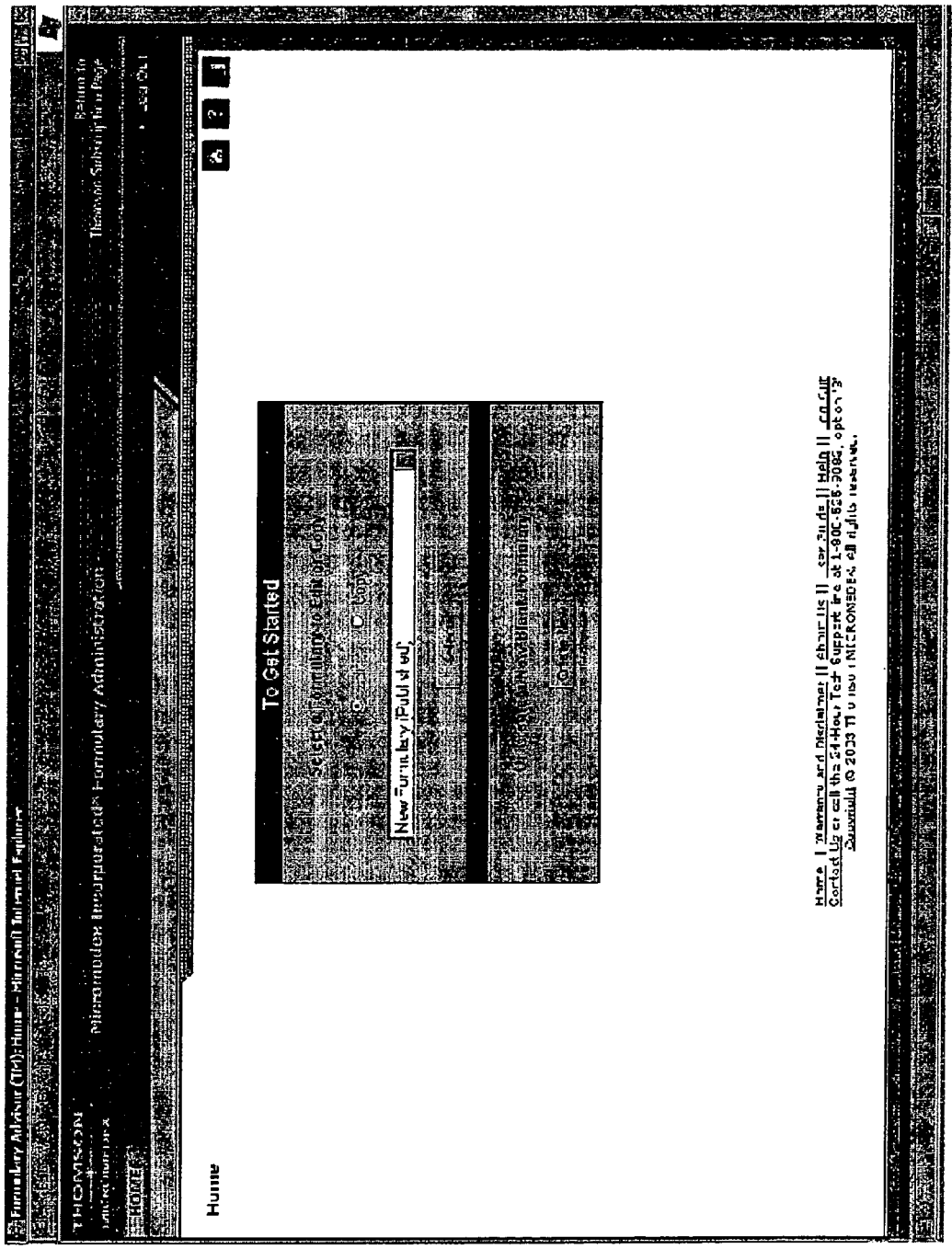
FIGS. 9A, 9B, 9C and 9D depict screenshots according to a preferred embodiment of the invention.
Figure 9B:
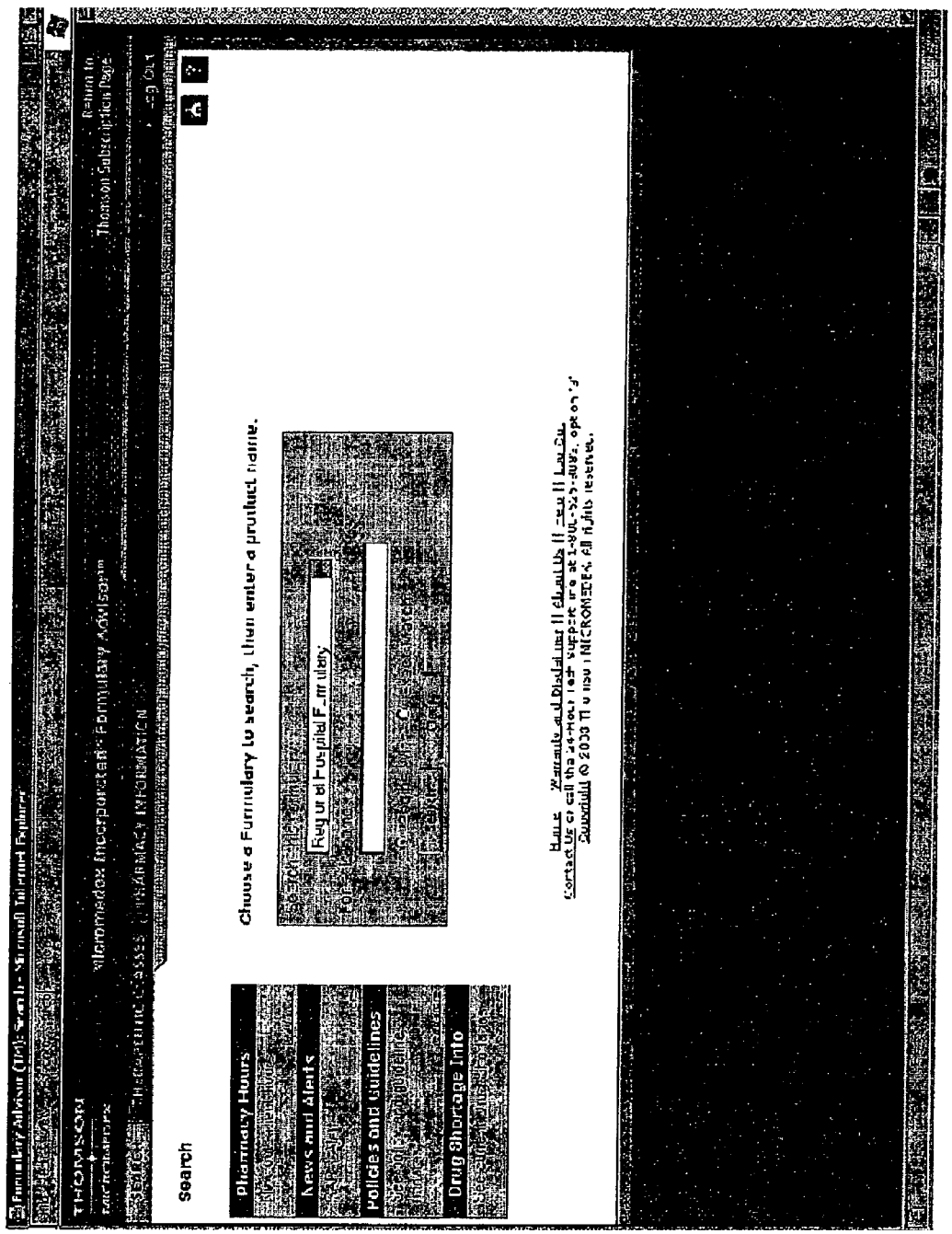
Figure 9C:
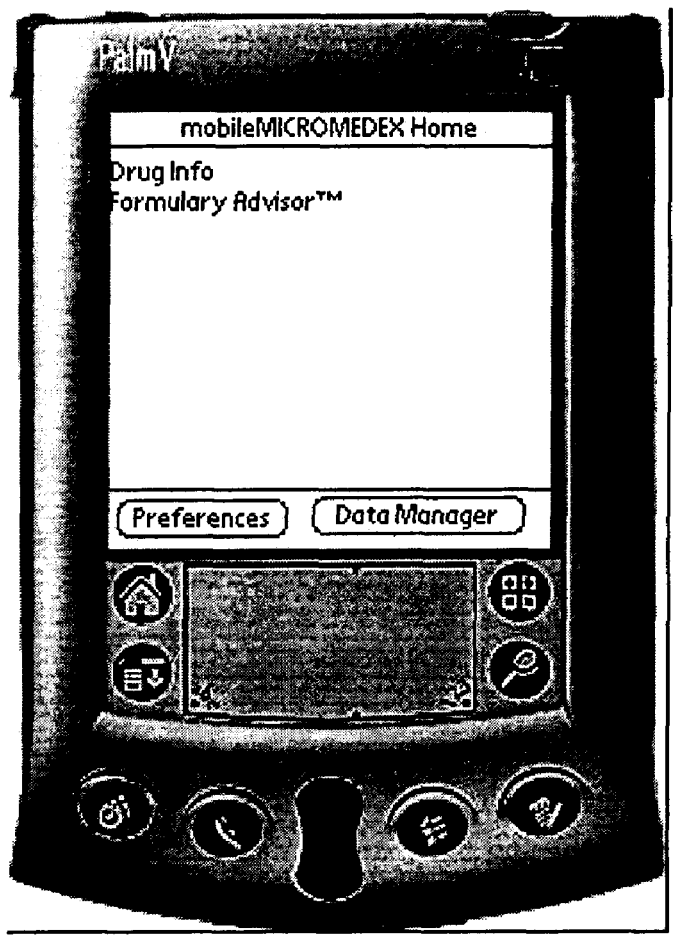
Figure 9D:
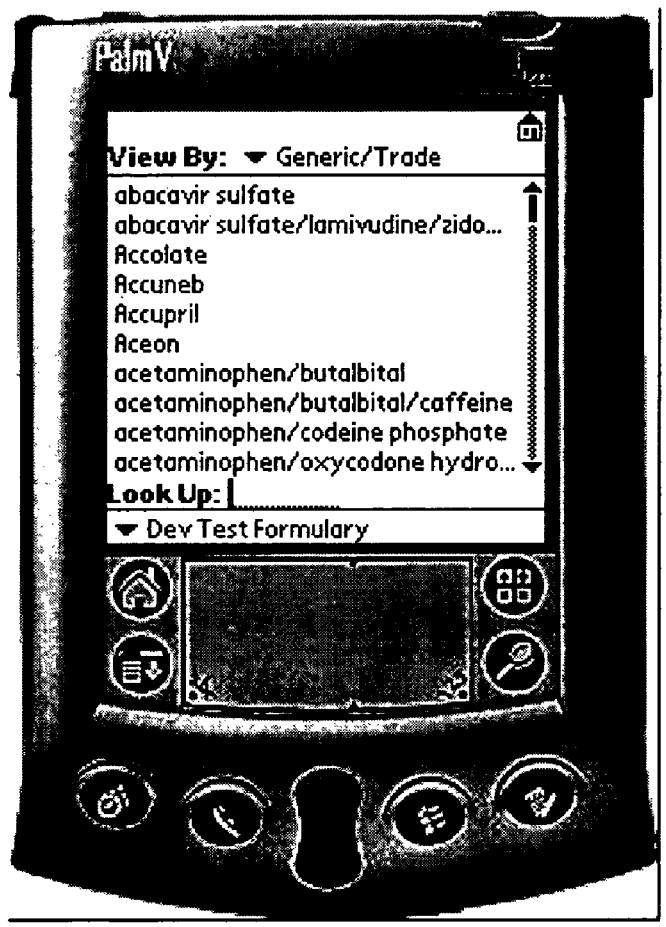

When the system authorizes access to a user, the system recognizes the user and provides a customized view appropriate to the user, for example the user type, utilizing the user's preferences, or favorites services. For example, an administrator user of a formulary product, is provided the view shown in FIG. 9A, which provides access to the administrator's version of the formulary product. By contrast, a non-administrator, such as a medical provider, or other formulary product user is provided the view shown in FIG. 9B upon logging into the system. FIG. 9C shows the view displayed on a PDA of the formulary product. FIG. 9D shows the view of the system access screen on a PDA.

If the user is authorized, the user is provided a display, for example, a system home page, or user home page, offering the user several products. The user selects a product, preferably a product delivered by the system, such as a formulary, from the display. If the user searches the product, the user selects the search by entering search terms, such as keywords or indexing, which preferably is the search 500 of FIG. 5, the system performs a search and provides results which may be retrieved by a user. Retrieving the results is preferably provided by the functionality of Content Retrieval 520 of FIG. 5. The user may continue searching the product or may select another product. When the user is finished using the system or product, the user logs out. Each use of the system or product (s), for example, inputs entered in connection with search 500 or content retrieval 520 is logged by the system (step 330) and a log is provided (step 340), for example, in the form of a report, preferably the reports 60 of FIG. 1, and may be stored in association with a user, or with the user's group or organization. The information provided in step 340 may be customized by the administrator of a user group or organization to provide use information relevant to the organizations needs. For example, an organization may wish to be provided with information related to the log to obtained information (step 330), or another organization may wish to only be provided with the identity of a user (step 300). The information provided (step 340) also may be summarized and sent to customers. In addition, the information (step 340) may be collected to understand the usability of the product and for enhancing the Internet delivery system based on use or demographics and market conditions.

The search 500 generally by entering user inputted search criteria into the system and searching the databases for the entered search criteria. For example, the user may select certain databases or products to search, and certain criterion to search for in those selected databases or products. The system performs searches by methods such as those described in U.S. patent application Ser. No. 10/289,782 titled ELECTRONIC DOCUMENT REPOSITORY MANAGEMENT AND ACCESS SYSTEM, and filed Nov. 20, 2002. For example, the system searches certain selected records, collections of records, information from a selected source, or other attributes associated with a database item, or searches using keywords or according to table of contents hierarchy. Results of the search include lists of relevant data provided in a view customized according to the user, and according to the type of device on which the results are displayed. For example, a search result list displayed on a desktop computer monitor may include multiple references and editorial notes. However, the same search results list displayed on a portable device may be limited to only the underlying product or document according to the portable device display size limitations, and may not include extraneous information provided on a desktop computer monitor display. In addition, a user may define a display view according to their preferences, the preference data is associated with the user in the preferences service 700. If the user defines a customized display view, the user preferences are stored to the system and used each time the user accesses the system. A user may select a search result from the list to retrieve from the system. Content retrieval 520 typically involves obtaining the document image and displaying it in the API 85 using the common domain objects 90.

Figure 10A:
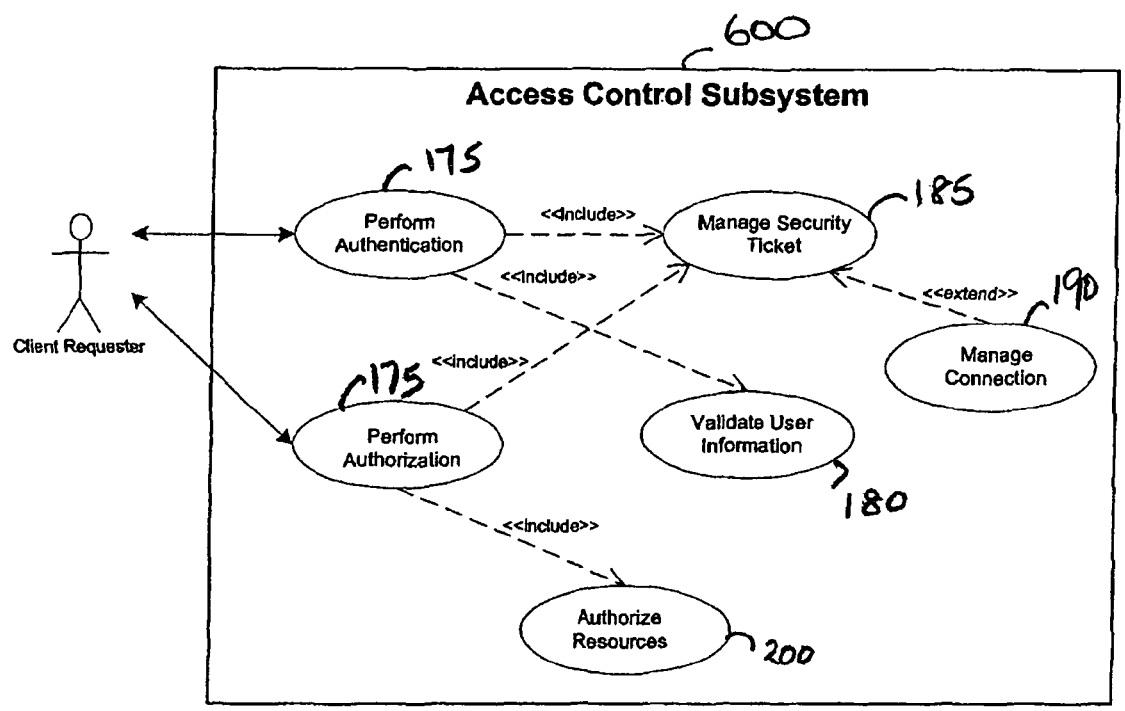
FIGS. 10A and 10B are a diagram an access control system according to an embodiment of the invention.

Referring to FIG. 10A, in a preferred embodiment of the invention, the log-in or access control procedure 600 is generally accomplished by performing authentication (step 175) using the methods described in reference to FIG. 8, for example, accomplished through the system webpage, and user authentication may be accomplished by system recognition of the user's IP address. When the user is authorized, the access control system validates the user information step 180, manages a security ticket step 185 or authorizes resources step 200.

Successful authentication of the user provides access to the system, for example, services, links, products, content databases and other functionality. The system stores the subscriber information in association with information such as the subscriber's IP address range, subscriber connection type, user names and/or passwords, contact information, product access or limitations, other user defined data associated with the user or product items, administrator, region, user preferences, favorites list or selected products. In addition, the subscription information may also contain or be associated with the subscription type including pricing or account type information, such as time based subscriptions, transaction-based subscriptions, pay per view, or block subscription.

Figure 10B:
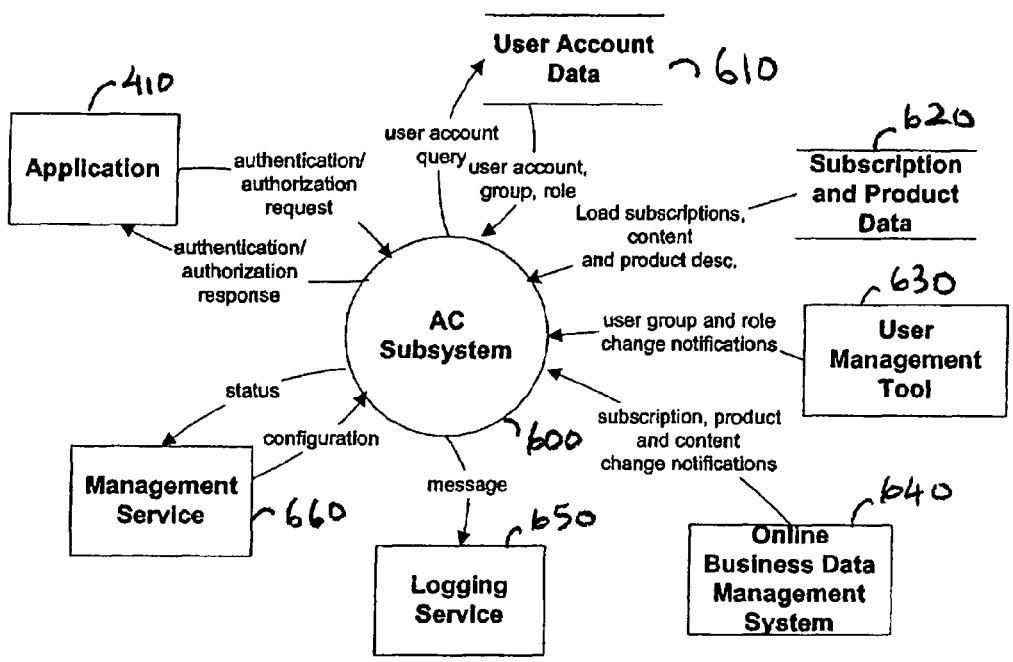

Referring to FIG. 10B, when the user is authorized by the access control subsystem 600, the access control system permits user access to the application 410, user account data 610, subscription and product data 620, user management tool 630, online business data management system 640, logging service 650 and management service 660. The user account data 610 includes for example the user account information, such as user type. The user account data 610 provides the system information as to user type so that a customized display appropriate to the user type is displayed when a particular user logs in. Examples of user types include users, such as: nurses, doctors, administrators, educators or prescribers. In addition, a user type may also be the type of device from which the system is accessed. Each user type may have a customized display, for example, customized look and feel of the user interface for the system, that has information or functionality related to the specific user or the needs of the user type. For example, an educator's customized display may include information or functionality relating to academics, literature or teaching materials, whereas a prescriber's customized display might include information or functionality relating to medicine or patient records, such as the formulary product screen shot example shown in FIG. 9B. In another embodiment of the invention, the administrator or administration subscriber may customize the user specific views as appropriate within the organization, such as the formulary product screen shot example shown in FIG. 9A. Other examples of customized displays include: displays appropriate to the access device type, such as a streamlined view for a device having a small screen, displays according to user or organization preference, print ready displays or displays in other languages. If the system does not determine that the user is a specific user type, the system provides the user with the default display.

Either one of the default display or customized user display or both of the display may include flexible or changeable displays which include useful information for a user entering the system such as, customer notification of current or pending changes to for example, documents, relevant rules, databases, functionality, new product information, scheduled maintenance. This useful information may also be sent as emails to each user group or customer.

Still referring to FIG. 10B, the subscription and product data 620 includes the user subscription information and product descriptions. The subscription and product data 620 provides the system with information related to the user's system access, for example, the electronic information products, content or other data items. Additionally, when the user is authenticated, the user management tool 630 and online business data management system 640 provide the user with information regarding user groups or roles and/or any subscription, product and content changes, respectively.

In one embodiment of the invention, the system is accessible directly by a PDA (personal digital assistant), mobile telephone, e-tablet, or other portable electronic device. A PDA user logs into the system as further described herein, using for example, handheld cradle synchronization, or wireless network. The system preferably recognizes that the system access point is a particular device type, and provides a customized view appropriate to the device type. For example, the content displayed on a mobile telephone screen or a PDA is provided with pared down content appropriate for the device layout and tailored navigation through the electronic information products or other data items provided by the system, as shown in FIG. 9C.

Figure 11:
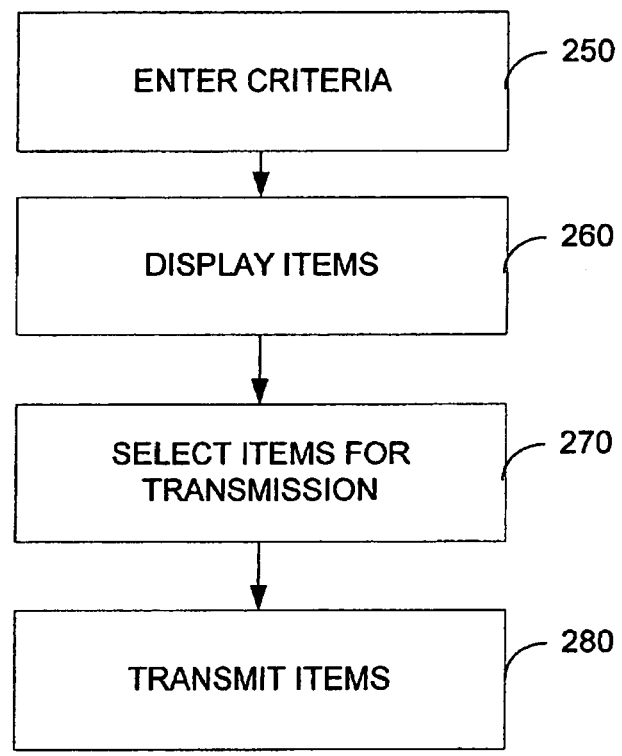
FIG. 11 is a flowchart of a method for transmitting results of the method and system according to an embodiment of the invention.

FIG. 11 depicts a flowchart of the system for transmitting system information, according to an embodiment of the invention. Information transmitted by the system includes, for example, electronic information products or other data items. The user accesses the system information by logging in as discussed herein, and enters criteria (step 250) to access the system information. Entering criteria is accomplished generally by entering text into the system, via for example, a keyboard, touch screen, or other device known in the art. The criteria may be for example a particular product, function or database in the system that the user wishes to access. In addition, the criteria may include search terms to be searched for within the selected product, function or database in the system. The criteria are processed by the system, for example by hierarchical menu selection, or searching as further described herein.

The items sought in the system information are displayed (step 260) for the user view. The items may be displayed (step 260) on the screen of the device the user is using to access the system, for example a computer 10. The user selects the displayed items for transmission (step 270), for example, by entering the appropriate item into the system, and the selected items are transmitted (step 280). The selected items may be transmitted to another device, for example a PDA, mobile telephone or other portable electronic device, so that the user may have access to selected system information from a portable device. This is particularly useful, for example, for using a formulary (such as the formulary management method and system described in U.S. patent application Ser. No. 10/675,236, titled NETWORK-BASED METHOD AND SYSTEM FOR MANAGING AND PROVIDING ACCESS TO A FORMULARY, filed concurrently herewith, so that a doctor or prescriber may access pharmaceutical information from a pocket-sized portable device that the user may use at the point of care. The selected items are transmitted via, for example, a wireless network, cradle or other transmission means known in the art or developed hereafter.

In another embodiment of the invention, a handheld device user synchronizes the handheld device with the system, for example, using a handheld cradle or wireless network, including a login procedure as described herein or other procedure providing user or subscription information. The system authorizes access to one or more content databases based on the login, user, or subscription information and transmits some or all of the content contained in the one or more authorized databases to the handheld device to store locally on the handheld device. The content stored to the handheld device may be searched and utilized by the handheld user as described herein.

Systems and components described herein may comprise software, firmware, hardware, or any combination(s) of software, firmware, or hardware suitable for the purposes described herein. Software and other components may reside on servers, workstations, personal computers, computerized tablets, PDAs, and other devices suitable for the purposes described herein. Software and other components may be accessible via local memory, via a network, via a browser, via client server or other application in an ASP (application service provider) context, or via other means suitable for the purposes described herein. Data structures described herein may comprise computer files, variables, programming arrays, programming structures, or any electronic information storage schemes or methods, or any combinations thereof, suitable for the purposes described herein.

While the invention has been described and illustrated in connection with preferred embodiments, many variations and modifications as will be evident to those skilled in this art may be made without departing from the spirit and scope of the invention, and the invention is thus not to be limited to the precise details of methodology or construction set forth above as such variations and modification are intended to be included within the scope of the invention.

What is claimed is:

1. An Internet delivery method delivering electronic information products to a plurality of users via the Internet, the method comprising:

storing a plurality of display formats in a database, said display formats including at least a default display format and one or more custom display formats;

storing information indicating whether one or more of said plurality of users is a specific type of user, wherein the specific type of user is authorized to access one or more content databases;

providing access to an authenticated user in a customized fashion, including displaying requested electronic product information to the authenticated user in accordance with the one or more custom display formats that are associated with the authenticated user;

delivering electronic product information to the authenticated user in accordance with the one or more customized display formats that are associated with the authenticated user;

determining, upon a valid authentication of a user from said plurality of users, whether the authenticated user is said specific type of user;

delivering, upon determination that the authenticated user is said specific type of user, a system display page formatted in a custom display format from the one or more custom display formats, said system display page configured to receive search criteria for one or more electronic information products;

delivering, upon determination that the authenticated user is not said specific type of user, the system display page formatted in said default display page format and configured to receive the search criteria for the one or more electronic information products;

receiving a request for an electronic information product from said one or more electronic information products;

formatting, upon determination that the authenticated user is said specific type of user, said electronic information product to a customized version corresponding to said custom display format via retrieving one or more information items from said one or more content databases;

delivering, upon determination that the authenticated user is said specific type of user, said customized version of said electronic information product; and delivering, upon determination that the authenticated user is not said specific type of user, said electronic information product formatted in said default display format.

2. The method of claim 1, wherein the information indicating whether the user is the specific type of user comprises subscription account information.

3. The method of claim 1, wherein there are a plurality of user types and a plurality of custom display formats, each custom display format from said plurality of custom display formats corresponding to at least one user type from said plurality of user types.

4. The method of claim 3, wherein said plurality of custom display formats comprises custom display formats in different languages.

5. The method of claim 1, wherein either one or both of the custom display format and the default display format includes flexible or changeable information.

6. The method of claim 1, wherein the customized version of the electronic information product is transmitted to a wireless device.

7. The method of claim 6, further comprising:
recognizing that the customized version of the electronic information product is to be transmitted to the wireless device; and
transmitting the customized version of the electronic information product formatted in a customized display format appropriate for the wireless device.

8. The method of claim 1, wherein the electronic information products comprises healthcare information.

9. The method of claim 1, wherein the user's use of the method is tracked.

10. An Internet delivery system adapted to deliver electronic information products to a plurality of users via the Internet, the system comprising:
one or more content databases storing data or other information for electronic information products; and
one or more modules configured to:
provide access to the plurality of users in a customized fashion, including displaying requested electronic information to the plurality of users in accordance with one or more custom display formats that are associated with one or more of the plurality of users;
deliver electronic information to the plurality of users in accordance with the one or more customized display formats that are associated with the plurality users;
determine, upon a valid authentication of a user from said plurality of users, whether the authenticated user is a specific type of user,
deliver, upon determination that the authenticated user is said type of user, a system display page formatted in a custom display format, said system display page configured to receive search criteria for one or more electronic information products;
deliver, upon determination that the authenticated user is not said specific type of user, the system display page formatted in a default display format and configured to receive the search criteria for the one or more electronic information products;
receive a request for an electronic information product from said one or more electronic information products listed on said system display page;
format, upon determination that the authenticated user is said specific type of user, said electronic information product to a customized version corresponding to said custom display format via retrieving one or more information items from said one or more content databases;
deliver, upon determination that the user is said specific type of user, said customized version of said electronic information product, and
deliver, upon determination that the user is not said specific type of user, said electronic information product formatted in a default display format.

11. The system of claim 10, wherein information indicating whether the authenticated user is said specific type of user comprises subscription account information.

12. The system of claim 10, wherein there are a plurality of user types and a plurality of custom display formats, each custom display format from said plurality of custom display formats corresponding to at least one user type from said plurality of user types.

13. The system of claim 12, wherein the plurality of custom display formats comprises custom display formats in different languages.

14. The system of claim 10, wherein either one or both of the custom display format and the default display format includes flexible or changeable information.

15. The system of claim 10, wherein the electronic information product is transmitted to a wireless receiving device.

16. The system of claim 15, wherein electronic information product is transmitted wirelessly.

17. The system of claim 15, wherein the electronic information product is transmitted by cradle synchronization.

18. The system of claim 10, wherein said one or more modules are further configured to perform healthcare related functionality and deliver healthcare information.

19. The system of claim 10, wherein the user's use of the system is tracked.

20. The method of claim 1, wherein the custom display format includes a customized interface providing access to one or more databases, products, or functions associated with a set of subscription accounts of the identified specific type of user.

21. The method of claim 1, wherein the customized version of the electronic information product includes information gathered from a group consisting of a Physicians Desk Reference content database, proprietary pharmaceutical databases, and healthcare related databases.

22. The method of claim 2, wherein the subscription account information includes authorization to access one or more functions associated with the specific type of user, wherein the one or more functions are selected from a group consisting of pharmaceutical inventory management, formulary management, continuing medical education, healthcare related web community servers, and pharmaceutical order and delivery.

23. The system of claim 10, wherein the one or more content databases have stored therein one or more sets of healthcare-related information and a plurality of display formats, the plurality of display formats including custom display formats associated with particular users of the Internet delivery system or categories of users of the healthcare information delivery system, and wherein the one or more modules include
a requesting module configured to receive a set of search criteria from registered users through the custom display format and search the one or more databases for healthcare-related information corresponding to the set of search criteria.

24. The system of claim 23, wherein the requesting module further comprises an interface to a formulary management system.

25. A computer-readable storage medium containing a set of executable instructions, which when executed by one or more processors, cause said one or more processors to implement a method comprising:
storing a plurality of display formats in a database, said display formats including at least a default display format and one or more custom display formats;
storing information indicating whether one or more of said plurality of users is a specific type of user, wherein the specific type of user is authorized to access one or more content databases;
providing access to an authenticated user in a customized fashion, including displaying requested electronic information to the authenticated user in accordance with the one or more custom display formats that are associated with the authenticated user;
delivering electronic information to the authenticated user in accordance with the one or more customized display formats that are associated with the authenticated user;
determining, upon a valid authentication of a user from said plurality of users, whether the authenticated user is said specific type of user;
delivering, upon determination that the authenticated user is said type of user, a system display page formatted in a custom display format from the one or more custom display formats, said system display page configured to receive search criteria for one or more electronic information products;
delivering, upon determination that the authenticated user is not said specific type of user, the system display page formatted in said default display page format and configured to receive the search criteria for the one or more electronic information products;
receiving a request for an electronic information product from said one or more electronic information products listed on said system display page;
formatting, upon determination that the authenticated user is said specific type of user, said electronic information product to a customized version corresponding to said custom display format via retrieving one or more information items from said one or more content databases;
delivering, upon determination that the authenticated user is said specific type of user, said customized version of said electronic information product; and
delivering, upon determination that the authenticated user is not said specific type of user, said electronic information product or another electronic information product formatted in said default display format.

26. The computer-readable storage medium of claim 25, wherein the custom display format includes presentation logic on how to create the customized version of the electronic information product.

27. The method of claim 1, wherein said customized electronic information product includes information associated with embedding said customized electronic information product in said display page.

28. The method of claim 1, wherein said formatting said electronic information product to said custom display format further includes:
accessing an application framework communicable with one or more services associated with said electronic information product, and
retrieving, via said application framework, information associated with said custom display format from said one or more services.

29. The system of claim 10, wherein said customized electronic information product includes information associated with embedding said customized electronic information product in said display page.

30. The system of claim 10, wherein said one or more modules are further configured to:
access an application framework communicable with one or more services associated with said electronic information product, and
retrieve, via said application framework, information associated with said custom display format from said one or more services.

31. The computer-readable storage medium of claim 25, wherein said customized electronic information product includes information associated with embedding said customized electronic information product in said display page.

32. The computer-readable storage medium of claim 25, wherein said formatting said electronic information product to said custom display format further includes:
accessing an application framework communicable with one or more services associated with said electronic information product, and
retrieving, via said application framework, information associated with said custom display format from said one or more services.

33. The Internet delivery method according to claim 1, wherein the electronic information product formatted in the default display format is configured to receive at least one response from the user.

34. The system according to claim 10, wherein the electronic information product formatted in the default display format is configured to receive at least one response from the user.

35. The computer-readable storage medium according to claim 25, wherein the electronic information product formatted in the default display format is configured to receive at least one response from the user.

* * * * *